United States Patent [19]
Bailey

[11] Patent Number: 5,777,483
[45] Date of Patent: Jul. 7, 1998

[54] SENSING DEVICE TO SENSE CONTAMINANTS IN WATER

[75] Inventor: David F. Bailey, Riverview, Fla.

[73] Assignee: Jack Baxter, Marco Island, Fla.

[21] Appl. No.: 654,639

[22] Filed: May 29, 1996

[51] Int. Cl.$^6$ ................................................ G01R 27/26
[52] U.S. Cl. ........................................ 324/686; 73/61.44
[58] Field of Search ............................... 340/603, 618, 340/620, 612; 73/49.2, 61.44, 61.51, 61.43; 324/686, 698, 675, 368; 361/292

[56] References Cited

U.S. PATENT DOCUMENTS

| | | | |
|---|---|---|---|
| 3,746,974 | 7/1973 | Stoakes | 324/686 |
| 3,753,092 | 8/1973 | Ludlow | 324/686 |
| 4,058,802 | 11/1977 | Meyers | 340/605 |
| 5,125,265 | 6/1992 | O'Connell | 324/664 |

Primary Examiner—Christine K. Oda
Attorney, Agent, or Firm—Arthur W. Fisher, III

[57] ABSTRACT

A sensing device to detect contaminants of known dielectric value such as hydrocarbons when present in a medium with a different dielectric value such as water comprising a plurality of capacitive members electrically connected to a sensor signal generator including a plurality of sensor channels corresponding to the plurality of capacitive members to generate a sensor signal corresponding to the dielectric value of the medium surrounding each of the plurality of capacitive members and a detect signal generator including a plurality of detect channels corresponding to the plurality of sensor channels to receive the sensor signal of the corresponding sensor channel and to generate a contaminant detection signal when each sensor signal from each sensor channel is within a predetermined range of the dielectric value of the contaminant to be monitored.

6 Claims, 4 Drawing Sheets

SENSING DEVICE TO SENSE CONTAMINANTS IN WATER

BACKGROUND OF THE INVENTION

1. Field of the Invention

A sensing device to detect a contaminants of known dielectric value such as hydrocarbons and to generate a contaminant detection signal in response thereto.

2. Description of the Prior Art

Oil spills, large and small, are among today's most environmentally damaging events. Even relatively small spills that normally go undetected can wreck havoc with the ecosystem. Early detection is vital in containing and cleaning up oil spills before such spills reach populated areas, protected coastal environments and inland waterways.

U.S. Pat. No. 4,058,802 describes a device for detecting the presence of contaminants, such as an oil spill, in a body of water. At a predetermined location in the body of water at least one detector station means is provided having at least one contaminant detector element. The contaminant detector element has a characteristic that changes for the condition of the presence of a contaminant impinging thereon. The characteristic may be a dimension thereof. Sensing means are provided to detect changes in the characteristic and to generate an information signal responsive to such changes in the information signal response to such changes in the characteristic. A transmitter means is provided for transmitting a transmission signal response to the information signal when there has been a change in the characteristic. The transmission signal is transmitted to regions remote the detector station means. At such regions remote from the detector station means there is provided a receiving station means which receives the transmission signal and provides an output signal such as a control signal or a visual or audible signal in response thereto.

U.S. Pat. No. 3,719,936 discloses a system for the detection of oil spillage in water including a housing adapted to be disposed in a partially submerged buoyant state in a body of water and having a plurality of ports to allow entry of water and oil that is present on the surface thereof. A selectively transmissive permeable membrane of the hydrophobic hypophylic type is disposed within the housing in liquid communication with the oil-water interface. Only oil is transmitted through the permeable membrane to a chamber within the housing having a sensor disposed therein to detect the presence of oil and to generate an output signal of the oil when detected. The sensor comprises a resistance temperature dependent electrical thermometer or mechanically actuable by the weight of oil within the chamber to generate the output signal. The chamber can be removed from the detection system to permit collection of oil samples for analysis to determine the nature and source of the contaminant. In addition, a plurality of chambers can be provided to permit the sequential collection of a corresponding plurality of oil samples over time. A marking material can also be released to visually mark the spill site.

U.S. Pat. No. 3,918,034 shows a detector unit and system for detecting and signaling the presence of an oil slick on the body of water. An oil sensing assembly consists of a hydrophobic, oleophilic oil sensing material secured to one end of a rod and a magnet secured to the opposite end of the rod, the rod extending into the central bore of a watertight ballasted shell which houses a battery powered transmitter. An adjustable magnetic reed switch is positioned in the housing for actuation by the magnet secured to the rod to initiate an output signal from the transmitter. A wire cage surrounds the oil sensing material. An antenna connected to the output of the transmitter extends upwardly from the wire cage. Arms having floats on their terminating ends extend laterally outwardly from the shell, the floats having sufficient flotation capacity to suspend the unit in the water. The oil sensing assembly incorporating the hydrophobic oil sensing material is sufficiently buoyant to float on the surface of the water. When the oil sensing material contacts oil floating on the surface of the water, the assembly sinks into the water, moving the target adjacent the reed switch to close it and initiate an output signal from the transmitter which is received by a corresponding receiver. The receiver activates an audio or visual alarm.

U.S. Pat. No. 3,719,936 teaches a system for the detection of oil spillage on water including a housing adapted to be disposed in a partially submerged buoyant state in a body of water and having a selectively transmissive member for transmission of oil to a chamber which includes a sensor for detecting the presence of oil therein and for providing an output indication of oil presence.

U.S. Pat. No. 3,603,952 describes sensing methods and apparatus for monitoring the surface condition of a body of water including floating sensor units deployed on the water surface employing reflected infrared radiation detectors to sense the presence of floating hydrocarbons from an oil spill or floating industrial waste, sewage or the like. Telemetry signals report the surface condition of the body of water to a central receiver unit.

SUMMARY OF THE INVENTION

The present invention relates to a sensing device to detect a contaminant of known dielectric value in a medium and to generate a contaminant detection signal in response thereto comprising a sensing means and a detection signal generator means.

The sensing means comprises an array of capacitive members where the number, size and relative disposition of the individual capacitive members are selected to eliminate false detection signals and minimize cross-talk while monitoring the medium. The array includes a first and second capacitive member each comprising a substantially horizontal flat capacitive element disposed in substantially parallel relationship relative to each other with the second capacitive member having a greater surface area than the first capacitive member, and a third and fourth capacitive member each comprising an upper substantially horizontal flat capacitive element and a lower substantially horizontal flat capacitive element and an intermediate substantially vertical flat capacitive element extending therebetween.

The detection signal generator means comprises a power supply, an oscillator, a sensor signal generator including a plurality of sensor channels to receive signals from the corresponding capacitive member and to generate a sensor signal corresponding to the value of the dielectric sensed or measured by each capacitive member and a detect signal generator including a plurality of detect channels corresponding to the plurality of sensor channels to receive the corresponding sensor signal therefrom and to generate a contaminant detection signal when each sensor signal from each sensor channel is within a predetermined range of the dielectric value of the contaminant being monitored.

In operation, the sensing device is properly positioned in the medium such as a body of water to be monitored. Each sensor channel will generate a sensor signal of a specific voltage dependent upon the dielectric value of the particular fluid covering the corresponding capacitive member. These sensor signal are then fed to the corresponding detect channel. When each sensor signal is within a predetermined range of the dielectric value of the contaminant being monitored, the sensing device will generate a contaminant detection signal providing an indication of the presence of the contaminant in the medium immediately adjacent the sensing device.

The invention accordingly comprises the features of construction, combination of elements, and arrangement of parts which will be exemplified in the construction hereinafter set forth, and the scope of the invention will be indicated in the claims.

BRIEF DESCRIPTION OF THE DRAWINGS

For a fuller understanding of the nature and object of the invention, reference should be had to the following detailed description taken in connection with the accompanying drawings in which.

Similar reference characters refer to similar parts throughout the several views of the drawings.

DETAILED DESCRIPTION OF THE PREFERRED EMBODIMENT

Figure 1:
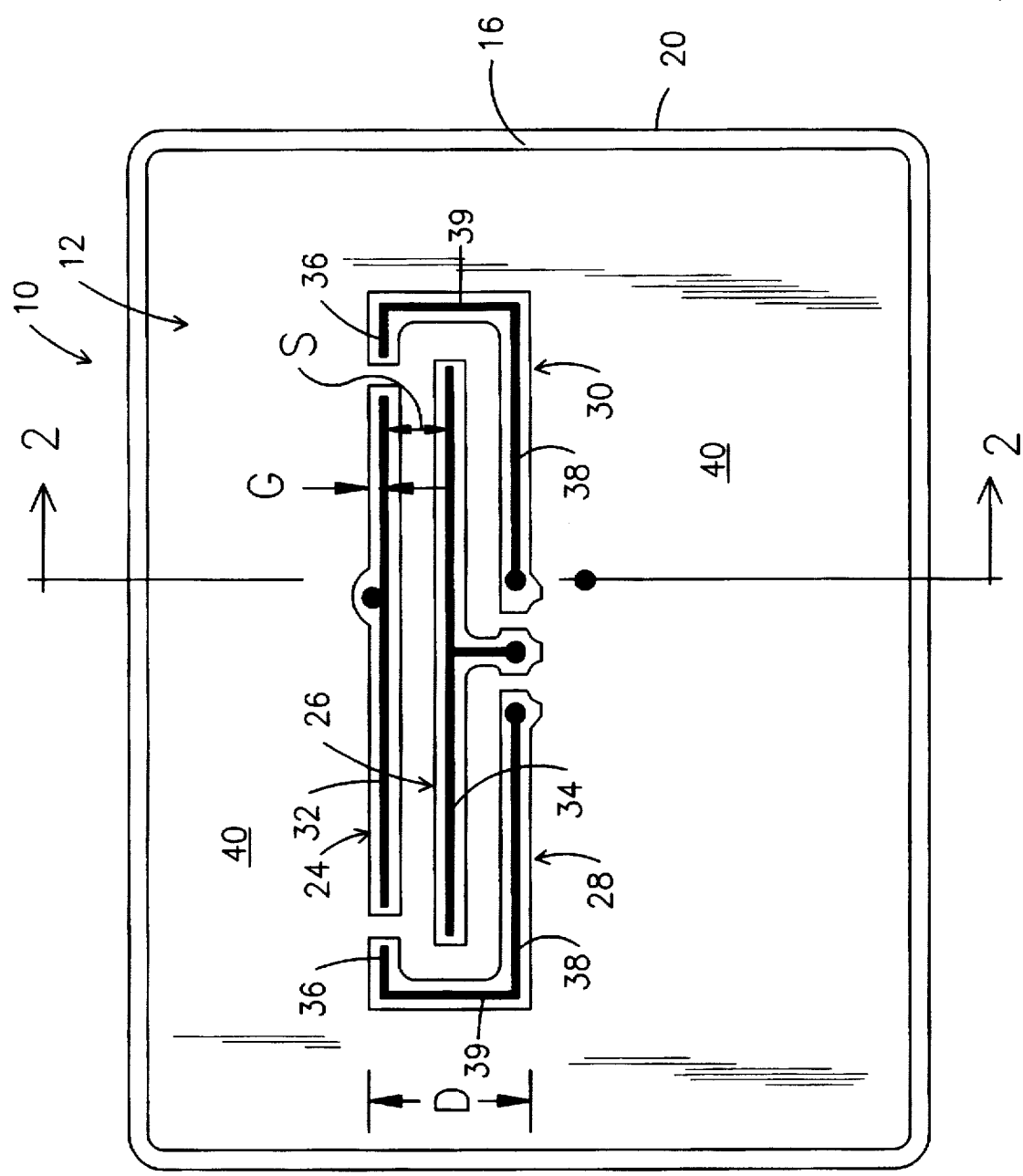
FIG. 1 is a front view of the sensing device of the present invention.
Figure 2:
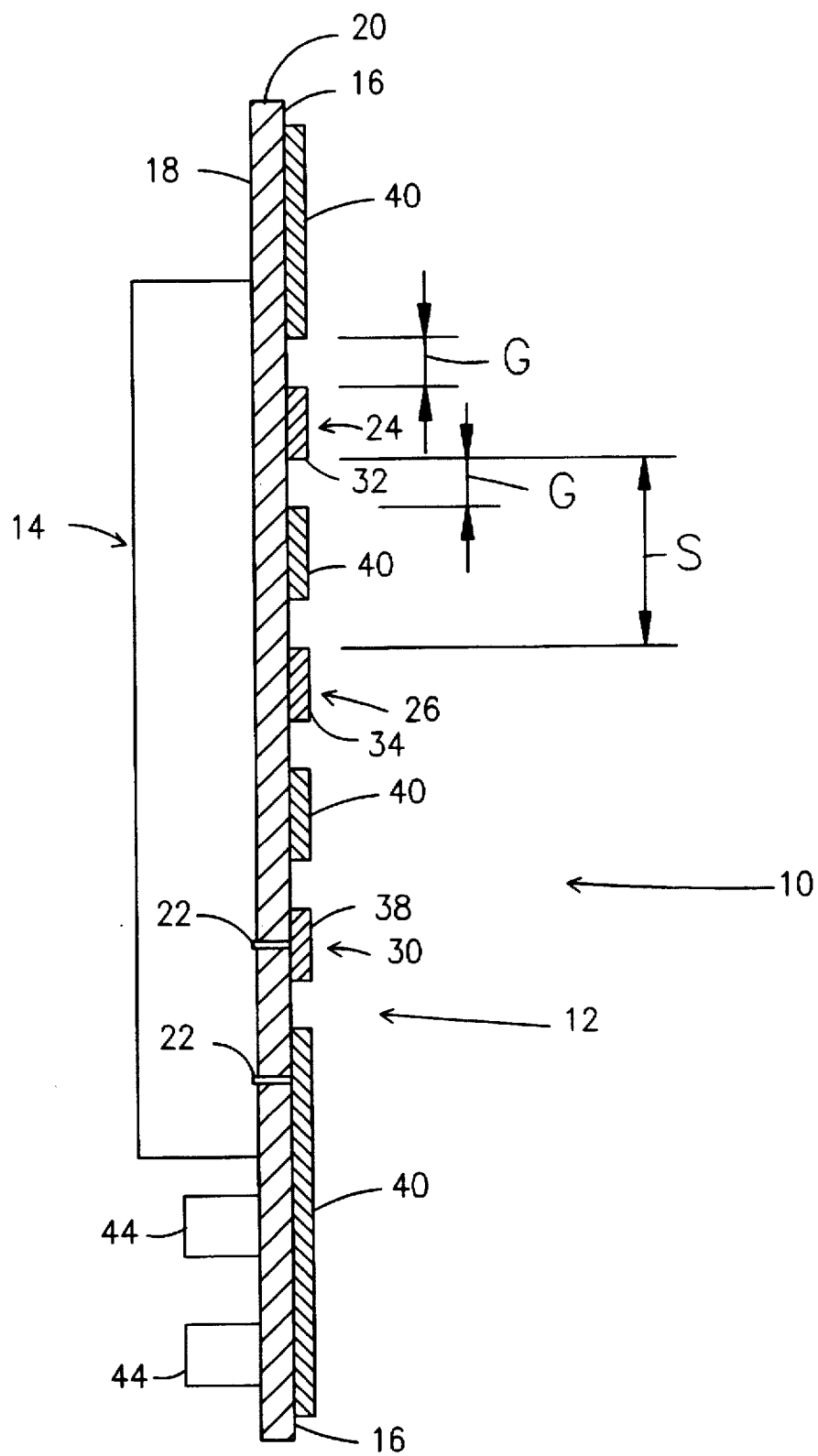
FIG. 2 is a cross-sectional top view of the sensing device of the present invention taken along line 2—2 of FIG. 1.
Figure 3:
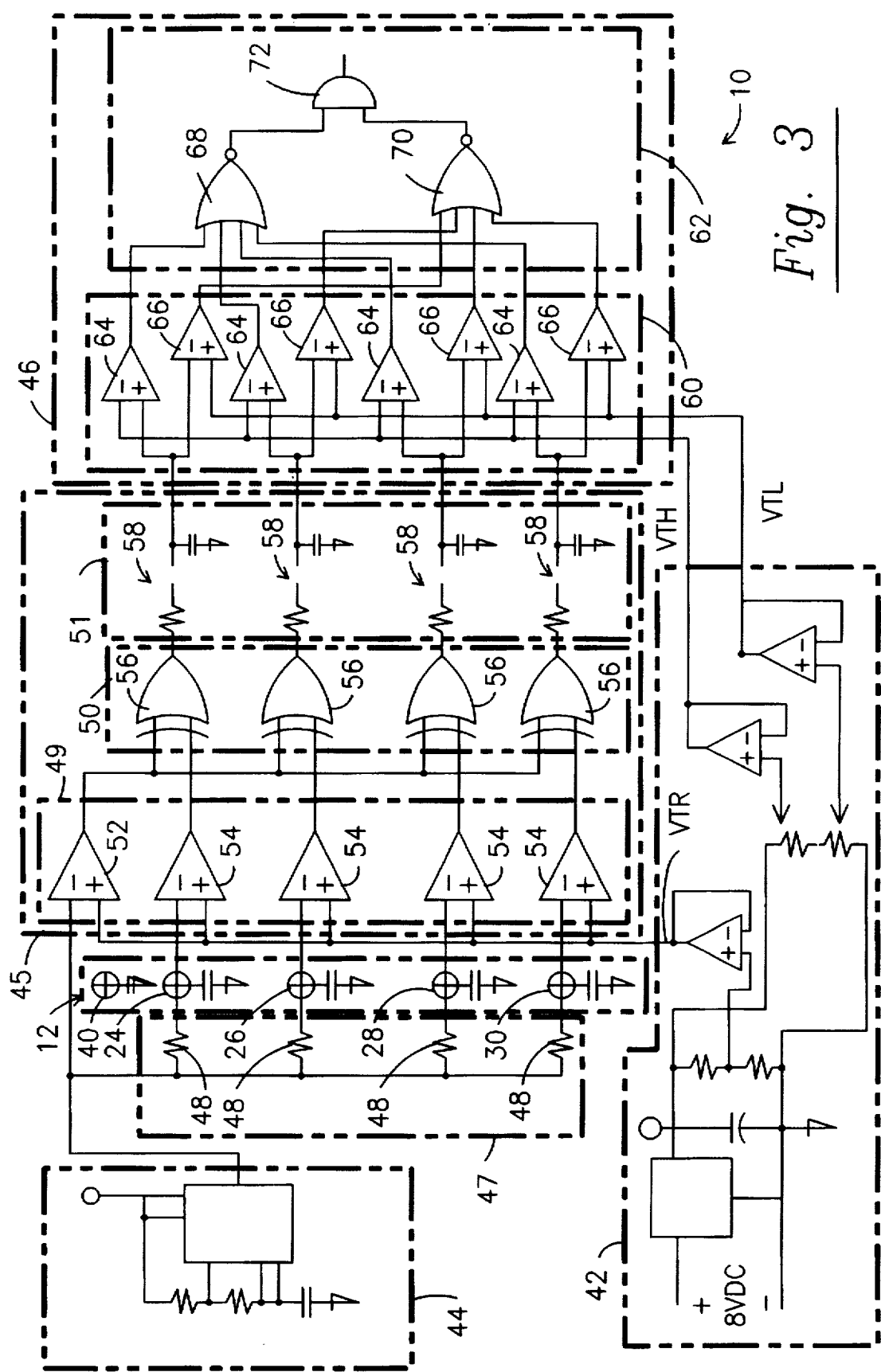
FIG. 3 is a schematic view of the sensing device of the present invention.

As best shown in FIGS. 1 through 3, the present invention relates to a sensing device generally indicated as 10 to detect a contaminant of known dielectric value and to generate a contaminant detection signal in response thereto. More specifically, the sensing device 10 comprises a sensing means generally indicated as 12 and a detection signal generator means generally indicated as 14 mounted on the front surface 16 and the rear surface 18 respectively of a substrate panel 20 and electrically coupled by plate through holes 22 each indicated as 22 formed in the substrate panel 20.

As previously suggested, the sensing device 10 of the present invention may be employed to detect the presence of hydrocarbons in water. The dielectric value of oil is approximately 1.5 to 3.0; while, the dielectric value of water is approximately 30. Thus, by submerging an array of capacitive members in a medium such as water, it is possible to measure the dielectric of the medium surrounding the array of capacitive members or electrodes to monitor or detect the presence of a contaminant of a known dielectric value. Thus, the sensing device 10 is particularly useful in a system or within an environment as described in copending application Ser. No. 08/391,424 filed Feb. 16, 1995 to detect contaminants.

As best shown in FIGS. 1 and 2, the sensing means 12 comprises an array of capacitive members including a first, second, third and fourth capacitive members generally indicated as 24, 26, 28 and 30 respectively. The number, size and relative disposition of the individual capacitive members 24, 26, 28 and 30 are selected to minimize false detection signals while monitoring the medium. The separation or spacing S between adjacent capacitive members 24, 26, 28 and 30 should be at least three times the gap G between ground 40 and of each capacitive member 24, 26, 28 and 30 but preferably the separation or spacing is at least four times the gap G. Furthermore, as described more fully hereinafter, the vertical distance D between the upper most capacitive surface and the lower most capacitive surface determines the minimum thickness of the contaminant required to generate a contaminant detection signal.

As best shown in FIG. 1, the first capacitive member 24 and the second capacitive member 26 comprise a substantially horizontal flat capacitive element indicated as 32 and 34 respectively disposed in substantially parallel relationship relative to each other with the second capacitive member 26 having a greater surface area than the first capacitive member 24. The third capacitive member and the fourth capacitive member 28 and 30 each comprises an upper substantially horizontal flat capacitive element 36 and a lower substantially horizontal flat capacitive element 38 and an intermediate substantially vertical flat capacitive element 39 extending therebetween. The common ground is shown 40.

As shown in FIG. 1, the upper and lower substantially horizontal capacitive elements 36 and 38 are substantially parallel to the substantially horizontal flat capacitive elements 32 and 34; while, the intermediate substantially vertical flat capacitive elements 39 are inclined relative to the substantial horizontal flat capacitive elements 32 and 34, and upper and lower substantially horizontal flat capacitive element 36 and 38.

Figure 4:
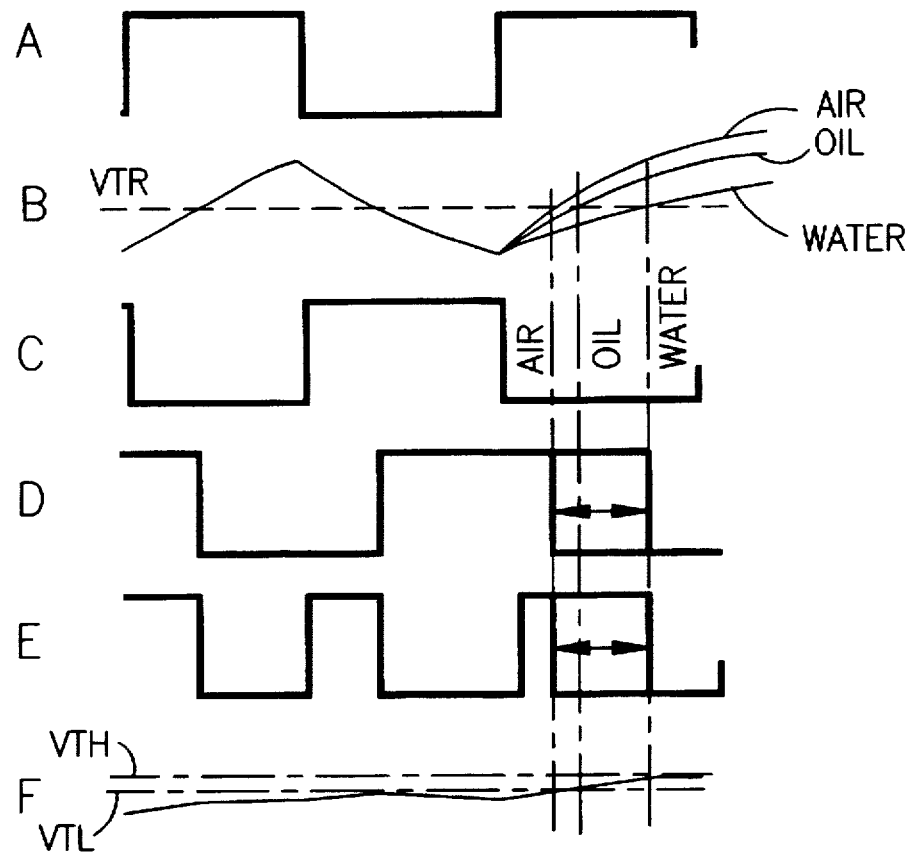
FIG. 4 is timing diagram of the sensing device of the present invention depicting the various component output voltages.

As shown in FIGS. 2 and 3, the detection signal generator means 14, comprises a power supply 42 to supply direct current to the electronic components and an oscillator 44 to provide a square voltage signal depicted as A in FIG. 4 and a sensor signal generator 45 including a plurality of sensor channels corresponding to the plurality of capacitive members 24, 26, 28 and 30 to receive the corresponding sensed signal therefrom and to generate a corresponding sensor signal depicted as F in FIG. 4 and a detect signal generator 46 including a plurality of detect channels corresponding to the plurality of sensor channels to receive the corresponding sensor signal therefrom and generate a contaminant detection signal when each sensor signal from each sensor channel is within a predetermined range of the dielectric value of the contaminant to be monitored.

As shown in FIG. 3, the output of oscillator 44 is fed to a resistor network 47 including a plurality of resistors each indicated as 48 corresponding to the first, second, third and fourth capacitive members 24, 26, 28 and 30 to cooperatively form a corresponding plurality of RC circuits and to the sensor signal generator 45.

As shown in FIG. 3, the sensor signal generator 45 comprises a sensor signal comparator means 49, a sensor signal mixer means 50 and a sensor signal filter means 51. The sensor signal comparator means 49 comprises a sensor comparator 52 to receive a threshold voltage from the power supply 42 and the output signal A from oscillator 44 and a plurality of capacitive sensing channel comparators each indicated as 54 to receive an output signal from the corresponding capacitive members 24, 26, 28 and 30 depicted as B in FIG. 4 and the threshold voltage from the power supply 42.

The sensor signal mixer means 50 comprises a plurality of exclusive OR gates or a sensor signal mixer each indicated as 56 to receive an output signal from the corresponding sensor signal comparator 52 depicted as C in FIG. 4 and an output signal from the corresponding capacitive sensing channel comparator 54 depicted as D in FIG. 4.

The sensor signal filter means 51 comprises a plurality of sensor signal filters each indicated as 58 to receive an output signal from the corresponding sensor signal mixer 56 depicted as E in FIG. 4.

As shown in FIG. 3, the output signals of the sensor signal generator 45 depicted as F in FIG. 4 is fed to the detection signal generator 46 comprising a detection signal comparator means 60 and a detect signal logic means 62. The detection signal comparator means 60 comprises a plurality of first and second comparators indicated as 64 and 66 respectively to cooperatively form a plurality of detect channels corresponding to the plurality of sensor channels to receive the output of the sensor channels. Each first comparator 64 is connected to the power supply 42 to receive an upper threshold voltage; while, each second comparator 66 is connected to the power supply 42 to receive a lower threshold voltage. The detect signal logic means 62 comprises a first NOR gate 68 and a second NOR gate 70 connected between an AND gate 72 and each first comparator 64 and each second comparator 66 respectively of each detect channel.

The operation of the sensing device 10 is best understood with reference to FIGS. 3 and 4. Specifically, the sensing device 10 is positioned in the medium to be monitored. When properly placed in a medium such as a body of water, the substrate panel 10 is vertically disposed with the first capacitive member 24 immersed in the water adjacent the water/atmosphere interface. The voltage of each sensor signal from each corresponding sensor channel depicted as F in FIG. 4 is dependent upon the dielectric value of the fluid covering or coating the corresponding capacitive members 24, 26, 28 and 30. The individual sensor signals are then compared in the corresponding detect channel with both a high threshold voltage VTH and a low threshold voltage VTL from the power supply 42.

As shown in FIG. 3, the high threshold voltage VTH and low threshold voltage VTL are adjustable to vary the voltage values corresponding to the values dictated by the dielectric value of the contaminant being monitored.

Each detect channel will generate a first detect signal when the corresponding sensor signal is less than the high threshold voltage VTH and a second detect signal when the corresponding sensor signal is greater than the low threshold voltage VTL. The detect signal logic means 62 will generate the contaminant detection signal to provide an indication of the presence of the contaminant in the medium immediately adjacent the sensing device 10 when the first and second detect signals from each detect channel are generated.

Since each detect channel must generate the first and second detect signals for the detect signal logic means 62 to generate the contaminant detection signal, the thickness of the contaminant in the medium at the sensing device 10 must be at least as great as the distance D.

It will thus be seen that the objects set forth above, among those made apparent from the preceding description are efficiently attained and since certain changes may be made in the above construction without departing from the scope of the invention, it is intended that all matter contained in the above description or shown in the accompanying drawing shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,

What is claimed is:

1. A sensing device to detect a contaminant to generate a contaminant detection signal in response thereto, said sensing device comprises a sensing means and a detection signal generator means mounted on the front surface and the rear surface respectively of a substrate panel and electrically coupled by plate through holes formed in said substrate panel, said sensing means comprises an array of capacitive members including a first, second, third and fourth capacitive members, the separation between adjacent capacitive members at least three times the gap between a ground and each said capacitive member, the vertical distance between the upper most capacitive surface and the lower most capacitive surface determines the minimum thickness of the contaminant requirement to generate said contaminant detection signal, said first capacitive member and said second capacitive member each comprises a substantially horizontal flat capacitive element disposed in substantially parallel relationship relative to each other with said second capacitive member having a greater surface area than said first capacitive member, said third capacitive member and said fourth capacitive member each comprises an upper substantially horizontal flat capacitive element and a lower substantially vertical flat capacitive element and an intermediate substantially vertical flat capacitive element extending therebetween, said upper and lower substantially horizontal capacitive elements are substantially parallel to said substantially horizontal flat capacitive elements and said intermediate substantially vertical flat capacitive elements are inclined relative to said substantial horizontal flat capacitive elements and said upper and lower substantially horizontal flat capacitive element.

2. The sensing device of claim 1 wherein said detection signal generator means comprises a power supply to supply direct current to the electronic components and an oscillator to provide a square voltage signal and a sensor signal generator including a plurality of sensor channels corresponding to said plurality of capacitive members to receive the corresponding sensed signal therefrom and to generate a corresponding sensor signal and a detect signal generator including aplurality of detect channels corresponding to said plurality of sensor channels to receive said corresponding sensor signal therefrom and generate a contaminant detection signal when each said sensor signal from each said sensor channel is within a predetermined range of the dielectric valve of the contaminant to be monitored.

3. The sensor device of claim 2 wherein the output of oscillator is fed to a resistor network including a plurality of resistors corresponding to said first, second, third and fourth capacitive members to cooperatively form a corresponding plurality of RC circuits and to said sensor signal generator.

4. The sensor device of claim 2 wherein the sensor signal generator comprises a sensor signal comparator means, a sensor signal mixer means and a sensor signal filter means. said sensor signal comparator means comprises a sensor comparator to receive a threshold voltage from the power supply and the output signal from said oscillarot and a plurality of capacitive sensing channel comparators to receive an output signal from the corresponding capacitive members and the threshold voltage from said power supply.

5. The sensor device of claim 4 wherein said sensor signal mixer means comprises a plurality of exclusive OR gates or a sensor signal mixer to receive an output signal from said corresponding sensor signal comparator and an output signal from said corresponding capacitive sensing channel comparator.

6. The sensor device of claim 5 wherein said sensor signal filter means comprises a plurality of sensor signal filters to receive an output signal from the corresponding sensor signal mixer.

* * * * *